United States Patent [19]

Fritz-Langhals

[11] Patent Number: 5,334,730

[45] Date of Patent: Aug. 2, 1994

[54] PROCESS FOR THE PREPARATION OF OPTICALLY ACTIVE CARBOXYLIC ACIDS AND AMIDE INTERMEDIATES

[75] Inventor: Elke Fritz-Langhals, Ottobrunn, Fed. Rep. of Germany

[73] Assignee: Consortium fur Elektrochemische Industrie GmbH, Fed. Rep. of Germany

[21] Appl. No.: 907,117

[22] Filed: Jul. 1, 1992

[30] Foreign Application Priority Data

Jul. 4, 1991 [DE] Fed. Rep. of Germany ....... 4122218

[51] Int. Cl.$^5$ ................. C07D 307/16; C07D 309/08; C07D 333/24; C07D 335/02
[52] U.S. Cl. ......................................... 549/13; 549/71; 549/72; 549/425; 549/484; 549/486; 549/487
[58] Field of Search ................. 549/13, 71, 72, 425, 549/486, 487, 484

[56] References Cited

FOREIGN PATENT DOCUMENTS

| 0355561 | 8/1989 | European Pat. Off. . |
| 0367515 | 10/1989 | European Pat. Off. . |
| 0382506 | 2/1990 | European Pat. Off. . |
| 1-216983 | 8/1989 | Japan . |

OTHER PUBLICATIONS

G. Stork et al., *Journal of the American Chemical Society*, vol. 99, No. 11, pp. 3851–3853 (1977).
O. Cervinka et al., *Collection Czechoslovak Chemical Communications*, 51, pp. 404–407 (1986).
P. Belanger et al., *Canadian Journal of Chemistry*, 61, pp. 1383–1386 (1983).
C. Grieco et al., *Archives of Biochemistry and Biophysics*, 194 No. 2, pp. 542–551 (1979).
R. Hill et al., *Journal of Organic Chemistry*, 27 pp. 921–924 (1962).
G. Claeson et al., *Arkiv for Kemi*, 26, No. 21, pp. 247–257 (1966).
T. Kaneko, et al., *Chemistry and Industry*, pp. 1187–1188, (1960).

H. Katsura, *Chemical Abstracts*, 56:9950a, abstract of *Nippon Kagaku Zasshi* 82, 92–2 (1961).
D. Roush et al., *Journal of the American Chemical Society*, 101, No. 11, pp. 2971–2981 (1979).
V. Boekelheide et al., *Journal of the American Chemical Society*, 80, pp. 3905–3908 (1958).
I. Kapovits et al., *Acta Chem. Acad. Sci. Hung.*, 34 pp. 79–86 (1962).
H. Silberman, *Journal of Organic Chemistry*, 25, pp. 151–153 (1960).
Wrobel, *Synthesis*, p. 452 (1987).
Freudenberg, *Ber. Dtsch. Chem. Ges.* 63, p. 2380 (1930).
R. Schwyzer et al., *Helv. Chem. Acta.*, 41, No. 139, pp. 1272–1286 (1958).

(List continued on next page.)

*Primary Examiner*—Richard L. Raymond
*Attorney, Agent, or Firm*—Burgess, Ryan & Wayne

[57] ABSTRACT

The present invention provides a process for the preparation of optically active carboxylic acids of the formula I* or II*

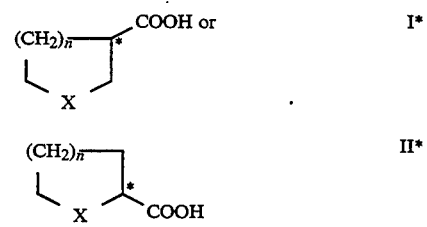

in which X is an oxygen or sulfur atom and n is 1 or 2. The process comprises reacting a racemic carboxylic acid I or II or its derivatives with an optically active 2-amino-carboxylic acid ester to give the diastereomeric carboxylic acid amides, separating the diastereomers and, after cleavage of the amide bond, isolating the optically active carboxylic acids of the general formula I* or II*. The invention also provides certain novel optically active carboxylic acid amides and a tetrahydrothiopyran-2-carboxylic acid.

24 Claims, No Drawings

OTHER PUBLICATIONS

W. Grassman et al., *Chem. Ber.*, 91, pp. 455–465 (1958).
D. A. Rowlands et al., *Journal of the Chemical Society*, pp. 1937–1938 (1952).
H. M. Flowers et al., *Biochem. J.*, 53, pp. 657–662 (1953).
M. Brenner et al., *Helvetica Chimica Acta*, 33 p. 568 (1950).
J. Rapp et al., *Biochemistry*, 5, No. 12, pp. 4100–4105 (1966).
R. Paul et al., *Compt. Rend.*, 208, pp. 359–361 (1939).
D. J. Pasto et al., *Journal of the American Chemical Society*, 87, No. 7, pp. 1515–1521 (1965).
J. March, "Advanced Organic Chemistry", 3rd ed. John Wiley & Sons, New York (1985).

PROCESS FOR THE PREPARATION OF OPTICALLY ACTIVE CARBOXYLIC ACIDS AND AMIDE INTERMEDIATES

BACKGROUND OF THE INVENTION

1) Field of the Invention

The invention relates to a process for the preparation of optically active carboxylic acids of the formula I* or II*

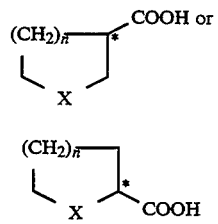

in which X is an oxygen or sulfur atom and n is 1 or 2.

2) Description of the Related Art

For the preparation of optically active carboxylic acids by resolution of racemates, up until now the racemic carboxylic acid to be separated was customarily reacted with an optically active amine and the diastereomeric salts formed were separated by fractional crystallization. This method was also used in the preparation of some of the abovementioned optically active heterocyclic carboxylic acids.

Thus, Bélanger et al (Can. J. Chem. 61 (1983) 1383) describe a process for the preparation of (R)- or (S)-tetrahydrofuran-2-carboxylic acid (formula II*: n=1, X=O with the aid of brucine or cinchonidine. However, these reagents cannot be employed because of their toxicity and their expense for obtaining relatively large amounts of the substance. Cervinka et al. (Collect. Czech. Chem. Commun. 51 (1986) 404) describe the resolution of the racemate of tetrahydrofuran-2-carboxylic acid with quinine. Using this method, however, only the (S)-enantiomer is obtained, whose yield after the required repeated recrystallization is only about 10%. In JP-A 01/216983, the resolution of the racemate of tetrahydrofuran-2-carboxylic acid using optically active 4-bromo- or 4-chloro-1-phenylethylamine is described. However, the origin of these optically active amines is not known.

The resolution of the racemate of tetrahydrothiophene-2-carboxylic acid (formula II: n=1, X=S) using brucine or cinchonidine (Claeson et al, Ark. Kemi 26 (1967) 247; Stork and Kreft III, J. Am. Chem. Soc. 99 (1977) 3851) and also using N-methyl-(S)-1-phenylethylamine (Cervinka et al., Collect. Czech. Chem. Commun. 51 (1986) 404) in each case only yielded one of the two enantiomers in moderate yields The same is true for the resolution of the racemate of (2H)-tetrahydropyran-2-carboxylic acid (formula II: n=2, X=O with quinine ((S)-enantiomer in 4 % yield, Cervinka et al., Collect. Czech. Chem. Commun. 51 (1986) 404), the resolution of the racemate of tetrahydrofuran-3-carboxylic acid (formula I: n=1, X=O with quinine (Katsura, Chem. Abstr. 56 (1962) 9950; Kaneko et al., Chem & Ind. 1960, 1187; Hill et al. J. Org. Chem. 27, (1962) 921) and the resolution of the racemate of tetrahydrothiophene-3-carboxylic acid (formula I: n=1, X=S) using N-methyl-(S)-1-phenylethylamine (Cervinka et al., Collect. Czech. Chem. Commun. 51 (1986) 404).

The above disadvantages stand in the way of the preparation of relatively large amounts of substance and restrict the possibility of using optically active heterocyclic carboxylic acids as synthetic building blocks, for example in liquid crystals (cf. EP-A 355561). Moreover, until now (2H)-tetrahydrothiopyran-2-carboxylic acid (formula II: n=2, X=S), (2H)-tetrahydropyran-3-carboxylic acid (formula I: n=2, X=O and (2H)-tetrahydrothiopyran-3-carboxylic acid (formula I, n=2, X=S) have not yet been prepared in optically active form. There is, however, a need for these last-mentioned hitherto unknown carboxylic acids, as these can also be used as building blocks for liquid crystals because of their structural relationship with the abovementioned known carboxylic acids.

The object of the invention was therefore to make available a simple process for obtaining the optically active compounds with the formulae I* and II*, with which the optical antipodes can be obtained in good yields in a simple manner.

SUMMARY OF THE INVENTION

This object is achieved by a process according to the invention in which, for the resolution of the racemate of the carboxylic acids, instead of the customary separation by crystallization of diastereomeric salts, a separation of the covalent linkage products between racemic carboxylic acids and optically active amines is carried out. Instead of the customarily used optically active amines, optically active 2-amino-carboxylic acid esters are used. Surprisingly, it has in particular been shown that carboxylic acid amides which are prepared by linkage of optically active 2-aminocarboxylic acid esters with racemic carboxylic acids of the general formulae I or II via an amide bond are particularly suitable for a diastereomer separation for the preparation of the optical antipodes of the carboxylic acids. The diastereomer separation succeeds with the above carboxylic acid amides in a particularly simple manner in high yields.

DESCRIPTION OF THE PREFERRED EMBODIMENT(S)

The present invention relates to a process for the preparation of optically active carboxylic acids of the formula I* or II*

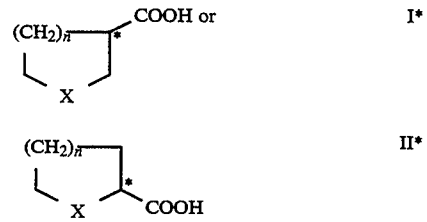

in which X is an oxygen or sulfur atom and n is 1 or 2, which comprises reacting a racemic carboxylic acid I or II or its derivatives with an optically active 2-aminocarboxylic acid ester to give the diastereomeric carboxylic acid amides, separating the diasteromers and, after cleavage of the amide bond, isolating the optically active carboxylic acids of the general formula I* or II*.

In another embodiment, the invention further relates to optically active carboxylic acid amides of the formulae IV* and V*

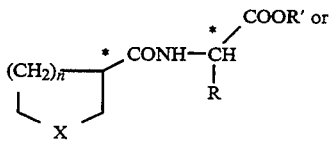

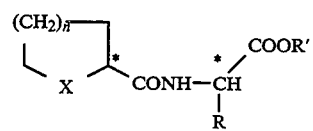

Finally, in a further embodiment the invention comprises optically active carboxylic acids of the formula I* or II*,

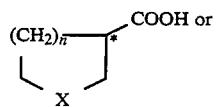

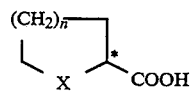

with X=S or S and n=1 or 2.

The racemic carboxylic acids of the general formula

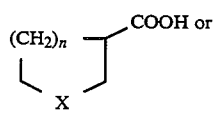

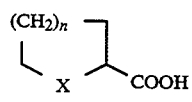

with X=S or S and n=1 or 2 can be prepared by methods known from the literature.

Tetrahydrofuran-2-carboxylic acid (formula II: n=1, X=S) can be prepared, for example, by hydrogenation of furan-2-carboxylic acid with Raney Nickel (Paul and Hilly, Compt. rend. 208 (1939) 359). Tetrahydrothiophene-2-carboxylic acid (formula II: n=1, X=S) is accessible by reaction of methyl 2,5-dibromovalerate with sodium sulfide and subsequent alkaline hydrolysis of the ester group (Cleason and Jonsson, Ark. Kemi 26 (1967) 247), (2H)-tetrahydropyran-2-carboxylic acid (formula II: n=2, X=S) can be obtained by oxidation of (2H)-2-hydroxymethyltetrahydropyran with chromium trioxide (Pasto and Serve, J. Am. Chem. Soc. 87 (1965) 1515), (2H)-tetrahydrothiopyran-2-carboxylic acid (formula II: n=2, X=S) can be prepared, for example, from 2,6-dibromohexanoic acid by ring closure with sodium sulfide (Roush et al., J. Am. Chem. Soc. 101 (1979) 2971).

Tetrahydrofuran-3-carboxylic acid (formula I: n=1, X=S) can be prepared by hydrogenation of furan-3-carboxylic acid with Raney Nickel (Boekelheide and Morrison, J. Am. Chem. Soc. 80 (1958) 3905), tetrahydrothiophene-3-carboxylic acid (formula I: n=1, X=S) is accessible by reaction of methyl 1,4-dibromobutane-2-carboxylate with sodium sulfide and subsequent alkaline hydrolysis of the ester group (Kapovits and Kucsman, Acta Chim. Acad. Sci. Hung. 34 (1962) 79), (2H)-tetrahydropyran-3-carboxylic acid (formula I: n=2, X=S) can be obtained by hydrogenation of 2,3-dihydro-(4H)-pyran-5-carboxylic acid with Raney Nickel (Silberman, J. Org. Chem. 25 (1960) 151), (2H)-tetrahydrothiopyran-3-carboxylic acid (formula I: n=2, X=S) can be prepared, for example, from ethyl 1,5-dibromopentane-2-carboxylate by ring closure with sodium sulfide and subsequent alkaline hydrolysis (Kapovits and Kucsman, Acta Chim. Acad. Sci. Hung. 34 (1962) 79).

For the reaction with the optically active 2-aminocarboxylic acid esters, apart from the racemic carboxylic acids of the general formula I or II, derivatives thereof such as acid halides, in particular acid chlorides, esters, anhydrides or amides can also be employed. Preferably, the acid chlorides of the racemic carboxylic acids of the general formula I or II are used. The acid chlorides are preferably prepared from the racemic carboxylic acids using thionyl chloride (Wróbel and Hejchman, Synthesis 1987, 452).

(S)- or (R)-2-Aminocarboxylic acid esters of the general formula III*

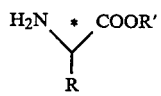

are suitable as the optically active component, the R radical being a linear, branched or cyclic $C_{1-6}$-alkyl radical in which a carbon atom is optionally replaced by an oxygen or sulfur atom or by the >NR" radical, where R" denotes a methyl or ethyl radical or R is a linear, branched or cyclic $C_{1-6}$-alkyl radical which is attached to the radicals —OH, —SH, —SCH₃, —NH₂, —COOR''', —CONH₂ or by a phenyl group which is optionally substituted by —CH₃, —OH, or —OCH₃, where R''' denotes a methyl, ethyl, n-propyl or 1-propyl group, or the radical R denotes a phenyl group which is unsubstituted or substituted by —CH₃, —OH or —OCH₃. The R' radical is a linear, branched or cyclic $C_{1-20}$-alkyl; or $C_{1-20}$-alkoxyalkyl radical which is optionally attached to a phenyl group, or is a phenyl radical.

Preferred R radicals are linear or branched $C_{-1-6}$-alkyl radicals, —CH₂OH, —CHOH(CH₃), —CH₂SH, —CH₂CH₂SCH₃, —CH₂(CH₂)₂NH₂, CH₂(CH₂)₃NH₂, —CH₂COOR''', —CH₂CONH₂, —CH₂CH₂COOR''', —CH₂CH₂CONH₂, phenyl, 4-hydroxy- and 4-methoxyphenyl and benzyl, where R''' has the above meaning. Particularly preferred R radicals are —CH₃, —CH(CH₃)₂, —CH₂CH(CH₃)₂, —CH₂CH₂SCH₃ and benzyl.

Preferred R' radicals are linear, branched or cyclic $C_{1-10}$-alkyl or $C_{1-10}$-alkoxyalkyl radicals; —CH₃, —CH₂OCH₃, —CH₂CH₃, —CH₂CH₂CH₃ and —CH(CH₃)₂ are particularly preferred.

Optically active 2-aminocarboxylic acid esters in the S configuration are to be mentioned in particular as optically active amine components of the general formula III*, since 2-aminocarboxylic acids and their derivatives having the S configuration occur naturally. Examples of these are (S)-alanine, (S)-valine, (S)-leucine, (S)-methionine and (S)-phenylalanine methyl esters.

The optically active 2-aminocarboxylic acid esters of the general formula III* can easily be prepared in the form of their hydrochlorides from the corresponding 2-aminocarboxylic acids, alcohols and HCl gas by methods known from the literature (Freudenberg et al., Bet. Dtsch. Chem. Ges. 63 (1930) 2380, Schwyzer et al., Helv. Chim. Acta 41 (1958 ) 1272, Grassman et al., Chem. Ber. 91 (1958 ) 455, Rowlands and Young, J. Chem. Soc. 1952, 1937, Flowers and Reith, Biochem. J. 53 (1953) 657). The preparation of methionine methyl ester hydrochloride can be carried out using thionyl chloride (Brenner et al., Helv. Chim. Acta 33 (1950) 568).

The reaction of the racemic carboxylic acids of the general formula I or II or their derivatives with the optically active 2-aminocarboxylic acid esters can be carried out directly without further additives or in the presence of an inert solvent such as toluene, tetrahydrofuran, methyl tert-butyl ether, ether or chlorinated hydrocarbons. Preferred solvents are tetrahydrofuran and methyl tert-butyl ether. If desired, basic auxiliaries such as carbonates, for example sodium carbonate, potassium carbonate or magnesium carbonate or tertiary amines, for example triethylamine or pyridine, can additionally be employed in the reaction of acid chlorides. When using tertiary amines, the reaction is preferably carried out in the presence of inert solvents in order to ensure adequate mixing in the presence of the sparingly soluble tert-amine hydrochloride formed.

The molar ratio of racemic carboxylic acid or its derivative to the optically active 2-aminocarboxylic acid esters is preferably between 1:2 and 2:1; the reaction components are particularly employed in equimolar amounts. The reaction is carried out with stirring, preferably at a temperature between about 20° and about 100° C., in particular between abut 20° and about 70° C. The reaction can be carried out after initial introduction of both reaction components, initial introduction of one reactant and metering of the second reactant or metering of both reaction components. Preferably, when working without addition of tertiary mines, one component is initially introduced and the second is metered in. In the case of addition of a tertiary amine, this is preferably initially introduced in a solvent together with the optically active 2-aminocarboxylic acid esters and the acid chloride is metered in. Depending on the reaction temperature and the intensity of stirring, the reaction time is between about 2 and about 20 hours.

When working without addition of tertiary amines, the reaction mixture is subjected to diastereomer separation without further working-up after termination of the reaction. If desired, the mixture can be diluted after completion of the reaction with an inert water-immiscible solvent such as methyl tert-butyl ether or toluene and treated with water or carbonate solution to remove acid. When using tertiary amines, it is expedient initially to filter these off in the form of their hydrochlorides after completion of the reaction and to subject the filtrate to diastereomer separation after washing with water, dilute hydrochloric acid and carbonate solution.

The diastereomer separation can be carried out by means of distillation, chromatography or by fractional crystallization. In a preferred embodiment of the process according to the invention, the diastereomer separation is carried out in a distillative manner.

Surprisingly, in the gas chromatographic investigation of the diastereomeric carboxylic acid amides of the formula IV or V

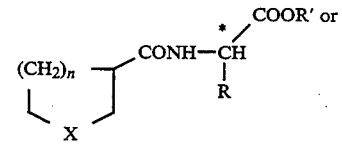

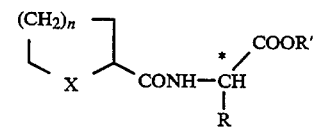

in which n, X, R and R' have the above meaning, extraordinarily large differences in the retention times were found which, as wan also experimentally confirmed with the diastereomers investigated here, correlate directly with the boiling point differences. A prior gas-chromatographic investigation is thus suitable in the present process for the planning of the subsequent preparative distillative separation (pressure/temperature, required plate number).

Since the diastereomers of the carboxylic acid amides of the general formula IV or V exhibit greatly different retention times in the gas-chromatographic separation and therefore also have large boiling point differences, the separation can be carried out using customary distillation equipment and columns. Columns which are suitable for vacuum distillation are preferred, such as, for example, columns having random beds (for example packing) or ordered internals (for example braided metal packing, Sulzer packing), or spinning band columns. Distillation equipment having a plate separation number between 1 and 100, in particular between 5 and 60, is particularly preferred.

The distillation can be carried out at atmospheric pressure or under reduced pressure. Processes under reduced pressure are preferred, since by means of this the material to be separated is less thermally stressed because of the reduction in boiling point. When working under reduced pressure, pressures between about 0.01 and about 50 tort are preferred, in particular pressures between about 0.1 and about 20 torr. The head temperature is preferably about 30° to about 180° C., particularly preferably about 80° to about 160° C. The bottom temperature is preferably about 50° to about 200° C.

In a further embodiment of the process according to the invention, the separation of the diastereomers of the general formula IV or V, as already described above, can be carried out by means of chromatographic methods, in particular in a gas-chromatographic manner. Columns suitable for this are, for example, quartz capillary columns containing silicones or polyethylene glycols, for example SE 54 or Carbowax 20M (Macherey-Nagel, W-5160 Duren-Rolsdorf), as stationary phases at temperatures between about 70° and about 250° C.

In a further embodiment of the process according to the invention, the diastereomers of the general formula IV or V can be separated by crystallization. Solvents which can be used are hydrocarbons, such as, for example, pentane, hexane, heptane, cyclohexane or methylcyclohexane, carbon tetrachloride or alternatively mixtures of the abovementioned solvents, or alcohols, for example methanol or ethanol. Preferred solvents are pentane, hexane, methylcyclohexane and methanol.

Preferably, the ester group of the compounds of the general formula IV or V is converted into the free carboxylic acid group by reacting with water or water and acid before diastereomer separation by crystallization. Hydrochloric acid at molar acid concentrations of 0.5 to 3M is preferred. 1N hydrochloric acid at temperatures between about 40° and about 70° C., in particular at temperatures between about 50° and about 60° C., is particularly preferred. A reaction in alkaline-aqueous solution at temperatures between about 30° and about 60° C., is also possible, for example using 0.1 to 2N NaOH or carbonate solution. Alkaline conditions, however, are less preferred compared to acidic conditions, since the mixture must initially be acidified for working-up and the salts formed in this process must be separated off. Additives which can be used which increase the solubility of the compounds of the general formulae IV and V in the reaction are water-soluble organic solvents such as tetrahydrofuran or 1,4-dioxane in amounts up to about 50% by volume or alcohols such as methanol, ethanol or isopropanol in amounts up to about 20% by volume. The reaction times are 12 hours to 4 days. Under the preferred conditions (1N HCl, 50°–60° C.), they are 2–3 days.

After the reaction, the acidic reaction solution is evaporated to isolate the free carboxylic acid of the general formula IV or V (R'=H) and recrystallized from a suitable solvent to separate the diastereomers. Suitable solvents include water and hydrochloric acid, methanol or ethanol or their mixtures with water, and furthermore hydrocarbons, carbon tetrachloride or mixtures of the two last-mentioned solvents. Examples of suitable hydrocarbons are pentane, hexane, heptane, cyclohexane, methylcyclohexane, xylene, toluene, benzene or mesitylene.

To isolate each of the optically active heterocyclic carboxylic acids of the general formula I* or II*, the amide bond is cleaved after diastereomer separation has been carried out. The cleavage is carried out in the aqueous phase with addition of about 5 to about 50 times the amount by weight of water. By addition of acid, preferably hydrochloric acid, a pH of between about 1 and about 6 is established. The cleavage is carried out at a temperature of preferably about 80° to about 200° C., in particular about 80° to about 120° C. Cleavage in 1N hydrochloric acid at a temperature between about 100° and about 120° C. is particularly preferred, since under these conditions the optically active 2-aminocarboxylic acid can be recovered without racemization.

To accelerate the cleavage reaction, if desired, metal salts can also be added in an amount of preferably about 1 to about 20 mol %, in particular about 4 to about 6 mol%, in each case relative to the isolated fraction of the carboxylic acid amides. Chlorides of divalent transition metals, for example $ZnCl_2$, $NiCl_2$ or $CuCl_2$, in particular $ZnCl_2$) are preferred in this case. The length of the cleavage reaction is in general between about 2 and about 10 days.

For working-up, the reaction mixture is evaporated after cleavage at a pH of 1 to 2 and the residue is digested in an inert solvent such as toluene, tetrahydrofuran or methyl tertbutyl ether to remove the optically active 2-aminocarboxylic acid. The insoluble residue consists of the optically active 2-aminocarboxylic acid in the form of its hydrochloride, which is recovered in this fashion and, as already described, can be converted into the corresponding ester again. After evaporation of the solvent, the organic phase is fractionally distilled at pressures between about 0.01 and about 20 torr to prepare the pure optically active carboxylic acid of the general formula I* or II*.

The optically active carboxylic acids prepared by the process according to the invention are suitable for use in the preparation of liquid crystalline compounds. The procedure according to the invention can additionally be used to prepare optically active amino acids in highly pure form using the optically active heterocyclic carboxylic acids obtained.

The examples illustrate the invention.

EXAMPLE 1

(Preparation of the heterocyclic carboxylic acid chlorides)

For conversion into the acid chloride, 440 g (3.79 mol) of tetrahydrofuran-2-carboxylic acid (formula II, X=O, n=1) in 400 ml of toluene were treated with 580 g (4.88 mol) of thionyl chloride in the course of 2–3 hours. The mixture was subsequently reacted at 65° C. for a further hour and the reaction product was obtained by fractional distillation, yield: 400 g (82%), b.p. 70°–72° C./17–20 torr (Lit. (Mooradian, J. Am. Chem. Soc. 71 (1949) 3372): 80°–81° C./30 torr), IR (Film): 1800s (CO) $cm^{-1}$.

The following were obtained analogously:

tetrahydrothiophene-2-carbonyl chloride (yield: 91%, b.p. 70° C./1.5 torr (Lit. (Wróbel and Hejchman, Synthesis 1987, 452): 113°–114° C./25 torr, IR (Film): 1786s (CO) $cm^{-1}$), (2H)-tetrahydropyran-2-carbonyl chloride (yield: 83%, b.p. 52°–56° C./1,1 torr, IR (Film): 1806s (CO) $cm^{-1}$, $^1$H-NMR (CDCl$_3$): δ=1.48–2.00 (m, 5H), 2.13 (m, 1H), 3.57 (mc, H-6), 4.07 and 4.27 (mc, H-6 and H-2)), (2H)-tetrahydrothiopyran-2-carbonyl chloride (yield: 56 g (92%), b.p. 75°–80° C./0.2 torr, IR (Film): 2930 m (CH), 2850 w (CH), 1789s (CO) $cm^{-1}$, $^1$H-NMR (CDCl$_3$): δ=1.56–1.98 (m, 4H), 2.00–2.19 (m, 1H), 2.19–2.31 (m, 1H), 2.41–2.61 (m, 1H), 2.72–2.91 (m, 1H), 3.79 (dd, CH)), tetrahydrofuran-3-carbonyl chloride (yield: 45%, b.p. 55°–58° C./15 torr, IR (Film): 1792s (CO) $cm^{-1}$, $^1$H-NMR (CDCl$_3$): δ=2.1–2.5 (m, CH$_2$), 3.55 (mc, CH), 3.82 (mc, CH), 3.87–4.03 (m, CH$_2$), 4.08 (mc, CH)).

EXAMPLE 2

(Preparation of the heterocyclic carboxamides of the formula IV or V with X=S or S and n=1 or 2)

617 g (3.68 mol) of (S)-valine methyl ester hydrochloride were suspended in about 2.2 l of tetrahydrofuran and 745 g (7.38 mol) of triethylamine were added. 451 g (3.35 mol) of tetrahydrofuran-2-carbonyl chloride in 200 ml of THF were added dropwise with stirring, the reaction temperature rising to about 65° C. After completion of the addition, the mixture was stirred at room temperature for a further 12 hours. The precipitate was filtered off with suction and thoroughly washed with tetrahydrofuran, and the combined organic phases were evaporated. The residue was dissolved in ether to remove excess (S)-valine methyl ester, shaken with water and dried in the customary manner. Vacuum distillation yields N-(2-tetrahydrofuroyl)-(S)-valine methyl ester (formula V with X=S, n=1, R=CH(CH$_3$)$_2$ and R'=CH$_3$) as a colorless liquid, b.p. 98°–103° C./0.01 torr, yield: 611 g (80%).

The following carboxamides were also obtained by this procedure:

N-(2-tetrahydrofuroyl)-(S)-valine ethyl ester (formula V with X=S, n=1, R=CH(CH$_3$)$_2$ and R'=C$_2$H$_5$), yield: 87%, b.p. 107°–110° C./0.01 torr;

N-(2-tetrahydrofuroyl)-(S)-alanine methyl ester (formula V with X=S, n=1, R=CH$_3$ and R'=CH$_3$), b.p. 92°–96° C./0.01 torr;

N-(2-tetrahydrofuroyl)-(S)-alanine ethyl ester (formula V with X=O, n=1, R=CH$_3$ and R'=CH$_2$H$_5$), b.p. 103°–107° C.;

N-(2-tetrahydrofuroyl)-(S)-leucine methyl ester (formula V with X=S, n=1, R=CH$_2$CH(CH$_3$)$_2$ and R'=CH$_3$), yield 80% b.p. 108°–115° C./0.01 torr;

N-(2-tetrahydrofuroyl)-(S)-methionine methyl ester (formula V with X=S, n=1, R=CH$_2$CH$_2$SCH$_3$ and R'=CH$_3$), b.p. 153°–156° C./0.1 torr;

N-(2-tetrahydrofuroyl)-(S)-phenylalanine methyl ester (formula V with X=S, n=1, R=CH$_2$-C$_6$H$_5$ and R'=CH$_3$), b.p. 162° C./0.01 torr;

N-(2-tetrahydrothiophenoyl)-(S)-valine methyl ester (formula V with X=S, n=1, R=CH(CH$_3$)$_2$ and R'=CH$_3$), m.p. 51°–58° C., b.p. 135°–144° C./0.05 torr;

N-(2-tetrahydrothiophenoyl)-(S)-alanine ethyl ester (formula V with X=S, n=1, R=CH$_3$ and R'=C$_2$H$_5$, m.p. 45°–50° C.;

N-(2-tetrahydrothiophenoyl)-(S)-leucine methyl ester (formula V with X=S, n=1, R=CH$_2$CH(CH$_3$)$_2$ and R'=CH$_3$), yield 66%;

N-((2H)-2-tetrahydropyranoyl)-(S)-valine methyl ester (formula V with X=S, n=2, R=CH(CH$_3$)$_2$ and R'=CH$_3$), yield 80%, b.p. 120°–125° C.;

N-((2H)-2-tetrahydropyranoyl))-(S)-leucine methyl ester (formula V with X=S, n=2, R=CH$_2$CH(CH$_3$)$_2$ and R'=CH$_3$), b.p. 116°–120° C./0.05 torr;

N-((2H)-2-tetrahydropyranoyl)-(S)-methionine methyl ester (formula V with X=S, n=2, R=CH$_2$CH$_2$SCH$_3$ and R'=CH$_3$), yield 83%, b.p. 152°–156° C./0.05 torr;

N-((2H)-2-tetrahydrothiopyranoyl)-(S)-valine methyl ester (formula V with X=S, n=2, R=CH(CH$_3$)$_2$ and R'=CH$_3$), yield 73%, m.p. 45°–50° C., b.p. 123°–132° C./0.05 torr;

N-((2H)-2-tetrahydrothiopyranoyl)-(S)-valine ethyl ester (formula V with X=S, n=2, R=CH(CH$_3$)$_2$ and R'=C$_2$H$_5$), yield 79%, b.p. 147°–155° C./0.2 torr;

N-((2H)-2-tetrahydrothiopyranoyl)-(S)-leucine methyl ester (formula V with X=S, n=2, R=CH$_2$CH(CH$_3$)$_2$ and R'=CH$_3$);

N-(3-tetrahydrofuroyl)-(S)-valine methyl ester (formula IV with X=S, n=1, R=CH(CH$_3$)$_2$ and R'=CH$_3$), b.p. 107°–109° C./0.01 torr;

N-(3-tetrahydrofuroyl)-(S)-leucine methyl ester (formula IV with X=S, n=1, R=CH$_2$CH(CH$_3$)$_2$ and R'=CH$_3$).

EXAMPLE 3

(N-(2-tetrahydrofuroyl)-(S)-valine methyl ester)

30.4 g (0.226 mol) of tetrahydrofuran-2-carbonyl chloride were heated to 50° C. with 41 g (0.246 mol) of (S)-valine methyl ester hydrochloride in 50 ml of toluene with stirring until evolution of HCl was complete (about 20 hours). The mixture was extracted by shaking with a little water and distilled. Yield of N-(2-tetrahydrofuroyl)-(S)-valine methyl ester (formula V with X=S, n=1, R=CH(CH$_3$)$_2$ and R'=CH$_3$): 48.4 g (94%).

EXAMPLE 4

(N-(2-tetrahydrothiophenoyl)-(S)-valine methyl ester)

134 g (0.89 mol) of tetrahydrothiophene-2-carbonyl chloride were added dropwise with stirring to a suspension of 210 g (1.26 mol) of (S)-valine methyl ester hydrochloride in 350 ml of toluene at a temperature of about 60° C. After addition was complete, the mixture was additionally stirred at 70° C. for 20 hours and separated from solid constituents, and the solution was shaken twice with about 30 ml of water each time and distilled. Yield 183 g (79%) of N-(2-tetrahydrothiophenoyl)-(S)-valine methyl ester (formula V with X=S, n=1, R=CH(CH$_3$)$_2$ and R'=CH$_3$), m.p. 55°–65° C., b.p. 115°–128° C./0.01 torr.

EXAMPLE 5

Gas-chromatographic investigation of the carboxamides of the formulae IV and V.

The carboxamides of the formulae IV and V were investigated by gas chromatography on the non-polar silicone phase SE 54 (25 m quartz capillary from Macherey-Nagel, W 5160 Düren-Rölsdorf; conditions: 2 min. isothermal at 70° C., heating rate 12° C./min to 250° C.) and the more polar phase Carbowax 20M (25 m quartz capillary from Macherey-Nagel, W 5160 Düren-Rölsdorf; conditions: 70°–230° C. with a heating rate of 8° C./min). The differences in the retention times—see Tab. 1 —were used to assess the distillation outlay required.

EXAMPLE 6

(Distillative separation of N-(2-tetrahydrofuroyl)-(S)-valine methyl ester)

The distillative separation of the carboxamide from Example 3 of the formula V with X=S, n=1, R=CH(CH$_3$)$_2$ and R'=CH$_3$ was performed using a 1 m packed column (packing: 4 mm glass spirals, internal diameter 5 cm) using a column head having an automatic liquid divider. Reflux ratio 5:1 to about 10:1; about 50 ml of distillate are taken off per hour. The distillation was carried out at pressures of 0.05 to 0.01 torr. The following fractions were obtained from 2.7 kg of carboxylic acid amide during distillation under the given conditions:

a) lower-boiling RS-diastereomer (V*(X=S, n=1, R=CH(CH$_3$)$_2$ and R'=CH$_3$)); optical purity in brackets: 86 g (99.9%), 673 g (99.0%, [α]$_D^{23}$ =+16.27 in substance), 220 g (98.5%), 192 g (97.0%);

b) middle fraction: 422 g of mixture;

c) higher-boiling SS-diastereomer (V* (X=S, n=1, R=CH(CH$_3$ )$_2$ and R'=CH$_3$)); 235 g (99.0%, [α]$_D^{23}$=−10.3 in substance), 419 g (99.8%). For boiling points see Table 1, for analytical data see Table 2 and for spectroscopic data see Table 3

EXAMPLE 7

(Distillative separation of N-(2-tetrahydrofuroyl)-(S)-valine methyl ester ).

In a 1 m packed column (packing 4 mm Wilson spirals; internal diameter 3 cm, reflux ratio 10:1, pressure 0.01 torr), 620 g of carboxylic acid amide from Example 3 of the formula V with X=S, n=1, R=CH(CH$_3$)$_2$ and R'=CH$_3$ yielded 206 g of the lower-boiling RS-diastereomer of the formula V* with X=S, n=1, R=CH(CH₃)₂ and R'=CH₃ (optical purity 95%) and 147 g of the higher-boiling SS-diastereomer of the formula V* with X=S, n=1, R=CH(CH₃)₂ and R'=CH₃ (optical purity 98%) in the distillation.

EXAMPLE 8

(Distillative separation of N-(2-tetrahydrofuroyl)-(S)-valine methyl ester)

In a 1 m packed column (packing: Sulzer stainless steel packing, internal diameter 5 cm, reflux ratio 10:1, pressure 0.01 torr), 1100 g of carboxylic acid amide from Example 3 of the formula V with X=0, n=1, R=CH(CH₃)₂ and R'=CH₃ yielded 468 g of the lower-boiling RS-diastereomer of the formula V* with X=0, n=1, R=CH(CH₃)₂ and R'=CH₃ (optimum purity 85%) and 137 g of the higher-boiling SS-diastereomer of the formula V* with X=S, n=1, R=CH(CH₃)₂ and R'=CH₃ (optimum purity 97%) in the distillation.

EXAMPLE 9

(Distillative separation of N-(2-tetrahydrothiophenoyl)-(S)-valine methyl ester).

183 g of carboxylic acid amide from Example 4 of the formula V with X=S, n=1, R=CH(CH₃)₂ and R'=CH₃ were distilled in a heated 1 m packed column (diameter 5cm, 5 mm glass helices, pressure 0.05 torr). The lower-boiling optically active component of the formula V* with X=S, n=1, R=CH(CH₃)₂ and R'=CH₃ (R,S-diastereomer) is obtained in an optical purity of 91% (by gas chromatography).

EXAMPLE 10

(Distillative separation of N-(2-tetrahydrothiophenoyl)-(S)-valine methyl ester)

The carboxylic acid amide (Example 2) of the formula V with X=S, n=1, R=CH(CH₃)₂ and R'=CH₃ was distilled in a spinning band column. The lower-boiling RS-diastereomer was obtained at 0.05 torr and a boiling temperature of 110°-117° C. in an optical purity of 100% (by gas chromatography). $[\alpha]_D^{23} = -14.07$, c=1.0 (CHCl₃). M.p. 60°-62° C.

EXAMPLE 11

(Distillative separation of N-((2H)-2-tetrahydrothiopyranoyl)-(S-)-valine methyl ester)

105 g of carboxylic acid amide (Example 2) of the formula V with X=S, n=2, R=CH(CH₃)₂ and R'=CH₃ were distilled at 0.01 torr in a heated Widmer column (length 30 cm). The lower-boiling (b.p. 134° C.) optically active component of the formula V* with X=S, n=2, R=CH(CH₃)₂ and R'=CH₃ was obtained in an optical purity of 62%.

EXAMPLE 12

(Distillative separation)

The optically active carboxylic acid amides V* with X=O, n=1, R=CH(CH₃)₂ and R'=C₂H₅; V* with X=S, n=1, R=CH₃ and R'=CH₃; V* with X=S, n=1, R=CH₃ and R'=C₂H₅; V* with X=S, n=1, R=CH₂CH(CH₃)₂ and R'=CH₃; V* with X=S, n=2, R=CH(CH₃)₂ and R'=CH₃; (lower-boiling diastereomer: $[\alpha]_D^{22} = +51.4$, c=1.02 (CHCl₃); higher-boiling diastereomer: $[\alpha]_D^{21} = -16.7$, c=1.02 (CHCl₃)) and IV* with X=S, n=1, R=CH(CH₃)₂ and R'=CH₃ were in each case obtained from the corresponding diastereomer mixtures IV and V (prepared according to Example 2) by distillation in a 1 m spinning band column (Teflon band, reflux ratio about 30:1, pressure about 0.01 torr).

The optical purities and boiling points obtained are found in Table 1. The analytical or spectroscopic data of the separated pairs of substances IV* and V* are found in Table 2 or Table 3.

EXAMPLE 13

(Isolation of optically active (R)-tetrahydrofuran-2-carboxylic acid).

100 g (0.437 mol) of carboxylic acid amide (prepared according to Example 6) of the formula V* with X=S, n=1, R=CH(CH₃)₂ and R'=CH₃ having a diastereomer ratio SS:RS=1.3:98.7 were stirred for about 4 days in 400 ml of 1N HCl at 100° C. with addition of about 3 g (22 mmol) of ZnCl₂. The reaction solution was evaporated and the residue was digested with methyl tert-butyl ether (MTBE). The filtered MTBE phase was fractionally distilled. 36 g (78%) of (R)-tetrahydrofuran-2-carboxylic acid (formula II* with X=S, n=1) of b.p. 83° C./0.3 torr, lit. (Pasto and Serve, J. Am. Chem. Soc. 87 (1965) 1515): 97°-100° C./1.05 torr were obtained. $[\alpha]_D^{27} = +33.3$, c=1.23 (CHCl₃); lit. (Bélanger et al., Can. J. Chem. 61 (1983) 1383): 30.1, c=1.21 (CHCl₃) for the (S)-enantiomer. $[\alpha]_D^{23} = +33.5$, $[\alpha]_D^{27} = +35.1$, c=1.07 (CHCl₃); lit. (Bélanger et al.): +30.4, c=1.01 (CHCl₃).

To determine the enantiomer ratio, the tetrahydrofuran-2-carboxylic acid obtained was reduced with LiAlH₄ to 2-tetrahydrofurfuryl alcohol and the latter was investigated by gas chromatography (chiral stationary phase Chiral-XE-60-S-Val from Chrompak, Munich). R:S=98.7:1.3 was found.

The filter residue of the MTBE phase, which consisted of (S)-valine hydrochloride, was dried in vacuo and then weighed 43 g (70%). After reaction with methanol/HCl and with trifluoroacetic anhydride, the optical purity of the recovered valine was determined by gas chromatography on Chiral-XE-60-S-Val. S:R=98.3:1.7 was found.

EXAMPLE 14

(Isolation of optically active tetrahydrothiophene-2-carboxylic acid)

5.2 g of carboxylic acid amide (isolated as in Example 9) of the formula V* with X=S, n=1, R=CH(CH₃)₂ and R'=CH₃ (lower-boiling RS-diastereomer with an optical purity of 91%) were heated at 100° C. for 30 hours in 100 ml of 1N hydrochloric acid with addition of 0.3 g of zinc chloride. The mixture was then evaporated, digested with toluene, filtered and distilled. 1.75 g (70%) of (R)-tetrahydrothiophene-2-carboxylic acid (formula II* with X=S and n=1) of b.p. 93°-94° C./0.1 torr were obtained. $[\alpha]_D^{22} = -112.4$ (c=0.442 (96 percent ethanol)) (Lit. (Claeson and Jonsson): $[\alpha]_D^{25} = -154.9$ (c=0.47 (96 percent ethanol)).

EXAMPLE 15

(Isolation of optically active (2H)-tetrahydropyran-2-carboxylic acid)

5.4 g of carboxylic acid amide (isolated as in Example 12) of the formula V* with X=O, n=2, R=CH(CH₃)₂ and R'=CH₃ (lower-boiling RS-diastereomer with an optical purity of 54%) were heated to 100° C. for 40 hours in 100 ml of 1N hydrochloric acid with addition of 0.35 g of zinc chloride. The mixture was then evaporated, digested with toluene, filtered and distilled. 2.25 g .(85%) of (R)-(2H)-tetrahydropyran-2-carboxylic acid (formula II* with X=S and n=2) of b.p. 79°-80° C./0.1 torr were obtained. $[\alpha]_D^{23} = +15.98$ (c=1.02 (CHCl$_3$)).

EXAMPLE 16

(Isolation of optically active (2H)-tetrahydrothiopyran-2-carboxylic acid)

2.0 g of carboxylic acid amide (isolated as in Example 11) of the formula V* with X=S, n=2, R=CH(CH$_3$)$_2$ and R'=CH$_3$ were heated at 100° C. for 40 hours in 20 ml of 2N hydrochloric acid with addition of 0.2 g of zinc chloride. (2H)-Tetrahydrothiopyran-2-carboxylic acid (formula II* with X=S and n=2) was obtained. IR (KBr): 2928 s (CH); 1704s (CO) cm$^{-1}$. $^1$H-NMR (CDCl$_3$): $\delta$=1.42-1.61 (m, 1H), 1.71-2.21 (m, 5H), 2.51-2.69 (m, 1H), 2.79-2.90 (m, 1H), 3.56 (dd, CH), 10.9 (s, broad, COOH).

EXAMPLE 17

(Crystallization of N-(2-(S)-tetrahydrofuroyl)-(S)-valine)

23.0 g (0.10 mol) of carboxylic acid amide (prepared as in Example 2) of the formula V with X=O, n=1, R=CH(CH$_3$)$_2$ and R'=CH$_3$ were stirred for about 3 days at 50°-60° C. in 100 ml of 1N HCl and the reaction solution was then evaporated to about 50 ml and left to cool. In this process, the SS-diastereomer V* with X=S, n=1, R=CH(CH$_3$)$_2$ and R'=H crystallized out in a yield of 12.7 g (59%). The diastereomeric purity was determined by gas chromatography after reaction to give the methyl ester and was >99.9%. M.p. 143°-149° C., IR (KBr): 3400m (NH), 2960 m (CH), 1733 s (CO), 1625 s (CO) cm$^{-1}$, $^1$H-NMR (CDCl$_3$): $\delta$=0.99 (2 d, 2CH$_3$), 1.92, 2.07, 2.30 (3 mc, each 2H), 3.94 (mc, 2H), 4.43, 4.54 (2 mc, each 1H), 7.23 (2 s, broad, NH), 9.6 (s, broad, COOH).

TABLE 1

GC retention times for the carboxylic acid amides of the formulae IV* and V* and the boiling points measured in the preparative separation and optical purities obtained.

| Pairs of compounds | | $t_{ret1}$[a] | $t_{ret2}$[b] | b.p.[c] | %*[d] | Type[e] |
|---|---|---|---|---|---|---|
| V* (X = O, n = 1, R = CH(CH$_3$)$_2$, R' = CH$_3$) | 1. | 10.54 | 16.68 | 98 | 99 (RS) | PC(6) |
| | 2. | 10.90 | 17.58 | 103 | 99.8 (SS) | PC(6) |
| V* (X = O, n = 1, R = CH(CH$_3$)$_2$, R' = C$_2$H$_5$) | 1. | 11.21 | 17.16 | 107 | 99 (RS) | SBC(12) |
| | 2. | 11.55 | 17.95 | 110 | 99.5 (SS) | SBC(12) |
| V*(X = O, n = 1, R = CH$_3$, R' = CH$_3$) | 1. | 9.29 | 16.33 | 92 | 99 (RS) | SBC(12) |
| | 2. | 9.53 | 16.93 | 95 | 99.5 (SS) | SBC(12) |
| V*(X = O, n = 1, R = CH$_3$, R' = C$_2$H$_5$) | 1. | 10.09 | 16.68 | 103 | 99 (RS) | SBC(12) |
| | 2. | 10.32 | 17.28 | 107 | 99.5 (SS) | SBC(12) |
| V*(X = O, n = 1, R = CH$_2$CH(CH$_3$)$_2$, R' = CH$_3$) | 1. | 11.56 | 18.57 | 108 | 99.8 (RS) | SBC(12) |
| | 2. | 11.86 | 19.07 | 115 | 95.1 (SS) | SBC(12) |
| V*(X = O, n = 1, R = (CH$_2$)$_2$SCH$_3$, R' = CH$_3$) | 1. | 14.23 | 21.13 | | | |
| | 2. | 14.35 | 21.98 | | | |
| V*(X = O, n = 1, R = CH$_2$—C$_6$H$_5$, R' = CH$_3$) | 1. | 15.06 | 25.51 | | | |
| | 2. | 15.29 | 27.05 | | | |
| V*(X = S, n = 1, R = CH(CH$_3$)$_2$, R' = CH$_3$) | 1. | 12.52 | 21.06 | 104 f) | 91.0 | PC(9) |
| | 2. | 12.88 | 22.19 | 110 –117 f) | 100.0 | SBC(10) |
| V*(X = S, n = 1, R = CH$_3$, R' = C$_2$H$_5$) | 1. | 11.92 | 20.98 | | | |
| | 2. | 12.17 | 21.74 | | | |
| V*(X = S, n = 1, R = CH$_2$CH(CH$_3$)$_2$, R' = CH$_3$) | 1. | 13.14 | 22.39 | | | |
| | 2. | 13.33 | 23.33 | | | |
| V*(X = O, n = 2, R =CH(CH$_3$)$_2$, R' = CH$_3$) | 1. | 11.68 | 18.62 | 77 | 90 | SBC(12) |
| | 2. | 11.88 | 19.08 | 82 | 94 | SBC(12) |
| V*(X = O, n = 2, R = CH$_2$CH(CH$_3$)$_2$, R' = CH$_3$) | 1. | 12.43 | 19.82 | | | |
| | 2. | 12.54 | 20.05 | | | |
| V*(X = O, n = 2, R = (CH$_2$)$_2$SCH$_3$, R' = CH$_3$) | 1. | 15.00 | 25.48 | | | |
| | 2. | 15.03 | 25.83 | | | |
| V*(X = S, n = 2, R = CH(CH$_3$)$_2$, R' = CH$_3$) | 1. | 13.00 | 21.82 | 134 f) | 62 | WC(11) |
| | 2. | 13.40 | 23.13 | | | |
| V*(X = S, n = 2, R = CH(CH$_3$)$_2$, R' = C$_2$H$_5$) | 1. | 13.65 | 21.89 | | | |
| | 2. | 14.01 | 23.14 | | | |
| V*(X = S, n = 2, R = CH$_3$, R' = CH$_3$) | 1. | — | 21.04 | | | |
| | 2. | — | 22.42 | | | |
| V*(X = S, n = 2, R = CH$_3$, R' = C$_2$H$_5$) | 1. | 13.65 | 21.78 | | | |
| | 2. | 14.01 | 22.69 | | | |
| V*(X = S), n = 2, R = CH$_2$CH(CH$_3$)$_2$, R' = CH$_3$) | 1. | 13.73 | 23.42 | | | |
| | 2. | 13.93 | 24.49 | | | |
| IV (X = O, n = 1, R = CH(CH$_3$)$_2$, R' = CH$_3$) | 1. | 11.50 | 20.51 | 107 | 73 | SBC(12) |
| | 2. | 11.57 | 20.67 | 109 | 72 | SBC(12) |
| IV*(X = O, n = 1, R = CH$_2$CH(CH$_3$)$_2$, R' = CH$_3$) | 1. | 12.34 | 22.37 | | | |
| | 2. | 12.35 | 22.54 | | | |

[a] GC retention time on SE 54, 25 m quartz capillary, 2 min isothermal at 70° C., heating rate 12° C./min to 250° C.;
[b] GC retention time on Carbowax 20M, 25 m quartz capillary, 70-230° C. with a heating rate of 8° C./min;
[c] At a pressure of about 0.01 to 0.05 torr;
[d] Optical purity in % on preparative separation;
[e] PC: packed column, SBC: 1 m spinning band column, WC: Widmer column, number in brackets gives no. of example;
f) The 2nd diastereomer is concentrated in the bottom.

TABLE 2

Analytical data of optically active carboxylic acid amides of the formulae IV* and V*.

| Product | Configuration[a] | | Elemental analysis |
|---|---|---|---|
| V*(X = O, n = 1, R = CH(CH$_3$)$_2$, R' = CH$_3$) | RS ($\cong$99) | C$_{11}$H$_{19}$NO$_4$ (229.3) | Calc. C 57.62 H 8.35 N 6.11 Found C 57.73 H 8.32 N 6.16 |

TABLE 2-continued

Analytical data of optically active carboxylic acid amides of the formulae IV* and V*.

| Product | Configuration[a] | | Elemental analysis | |
|---|---|---|---|---|
| | SS (≧99) | | | Found C 57.39 H 8.11 N 6.28 |
| V*(X = O, n = 1, R = CH(CH$_3$)$_2$, R' = CH$_2$H$_5$) | RS[a] (99.9) | $C_{12}H_{21}NO_4$ (243.3) | Calc. C 59.24 H 8.70 N 5.76 | Found C 59.41 H 8.70 N 5.88 |
| | SS (99.9) | | | Found C 59.26 H 8.75 N 5.77 |
| V*(X = O, n = 1, R = CH$_2$CH(CH$_3$)$_2$, R' = CH$_3$) | RS (99.8) | $C_{12}H_{21}NO_4$ (243.3) | Calc. C 59.24 H 8.70 N 5.76 | Found C 59.02 H 8.57 N 5.94 |
| | SS (95) | | | Found C 59.30 H 8.56 N 5.93 |
| V*(X = O, n = 1, R = CH$_3$ R' = C$_2$H$_5$) | RS (99.8) | $C_{10}H_{17}NO_4$ (215.3) | Calc. C 55.80 H 7.96 N 6.51 | Found C 55.73 H 8.01 N 6.87 |
| | SS (99.0) | | | Found C 56.03 H 7.95 N 6.94 |
| V*(X = S, n = 1, R = CH(CH$_3$)$_2$, R' = CH$_3$) | RS (100) | | | |
| V*(X = O, n = 2, R = CH(CH$_3$)$_2$, R' = CH$_3$) | RS (90.0) | $C_{12}H_{21}NO_4$ (243.3) | Calc. C 59.24 H 8.70 N 5.76 | Found C 59.46 H 8.97 N 5.73 |
| | SS (94.0) | | | Found C 59.22 H 8.96 N 6.10 |
| IV*(X = O, n = 1, R = CH(CH$_3$)$_2$, R' = CH$_3$ | 1.[b] (73) | $C_{11}H_{19}NO_4$ (229.3) | Calc. C 57.62 H 8.35 N 6.11 | Found C 56.04 H 7.96 N 5.96 |
| | 2. (72) | | | Found C 57.32 H 8.27 N 6.15 |

[a] Configuration, optical purity determined by gas chromatography in brackets,
[b] "1." ralates to the diastereomer of lower boiling point.

TABLE 3

Spectroscopic data of the carboxylic acid amides of the formulae IV* and V*

| Pair of compounds | | IR(film)/γ(cm$^{-1}$)[a] | $^1$H—NMR(CDCl$_3$)/δ (ppm) |
|---|---|---|---|
| V*(X = O, n = 1, R = CH(CH$_3$)$_2$, R' = CH$_3$ | 1. | 3405 w, 2960 m, 2873 m, 1743 s, 1687 s | 0.93 (t, J = 7 Hz, CH$_3$), 1.93 (mc, 2H), 2.0–2.4 (m, 3H), 3.75 (s, OCH$_3$), 3.90, 4.00 (2 mc, 2H-5), 4.41 (dd, α-CH), 4.53 (dd, H-2), 7.10, 7.15 (2s, broad, NH) |
| | 2. | 3405 w, 2960 m, 2873 m, 1743 s, 1687 s | 0.90, 1.91, 2.0–2.4, 3.75, 3.96 (mc, 2H-5), 4.39, 4.54, 7.13, 7.19[b] |
| V* (X = O, n = 1, R = CH(CH$_3$)$_2$, R' = C$_2$H$_5$) | 1. | 3415 w, 2963 w, 1740 s, 1688 s | 0.91 (t, J = 7 Hz, CH$_3$), 1.26 (t, J = 7.52 Hz, CH$_3$), 1.91 (mc, 2H), 2.0–2.4 (m, 3H), 3.90, 4.05 (2mc, 2H-5), 4.20 (mc, CH$_2$), 4.40 (dd, α-CH), 4.50 (dd, H-2), 7.10, 7.15 (2 s, broad, NH) |
| | 2. | 3412 w, 2963 m, 1740 s, 1686 s | 0.90, 1.26, 1.8–2.4 (m, 5H) 3.95 (mc, 2H-5), 4.20(q, J = 7.5 Hz,CH$_2$), 4.38, 4.50, 7.15, 7.20[b] |
| V*(X = O, n = 1, R = CH$_3$, R' = CH$_3$) | 1. | 3402 w, 3320 w, 2980 w, 2950 m, 2878 w 1745 s, 1672 s | 1.41 (d, J = 7.5 Hz, CH$_3$), 1.93 (mc, 2H). 2.0–2.4 (m, 3H), 3.75 (s, OCH$_3$), 3.83–4.08 (mc, 2H-5), 4.36 (dd, α-CH), 4.60 (mc, H-2) 7.18 (broad, NH) |
| | 2. | s.o. | 1.43, 1.94, 2.0–2.4, 3.75, 3.96, 4.39, 4.63[b] |
| V*(X = O, n = 1, R = CH$_3$, R' = C$_2$H$_5$) | 1. | 3404 w, 2980 m, 1740 s, 1674 s | 1.28 (t, J = 7 Hz, CH$_3$), 1.43 (d, J = 7.5 Hz, CH$_3$), 1.91, (m, 2H)2.0–2.4 (m, 3H), 3.90, 4.00 (2mc, 2H-5), 4.19 (q, J = 7 Hz,CH$_2$), 4.36 (dd, α-CH) 4.39 (mc, H-2), 7.10, 7.15 (2 s, broad, NH) |
| | 2. | 3404 w, 2981 m, 1740 s, 1675 s | 1.28, 1.41, 1.7–2.4 (m, 5H) 3.93 (mc, 2H-5), 4.21, 4.35, 4.54, 7.20, 7.30[b] |
| V*(X = O, n = 1, R = CH$_2$CH(CH$_3$)$_2$, R' = CH$_3$) | 1. | 3400 w, 2950 m, 1743 s, 1675 s | 0.95 (mc, 2CH$_3$), 1.50–1.73 (m, 3H), 1.93 (mc, CH$_2$), 2.05–2.15 (m, CH), 2.17–232 (m, CH), 3.73 |

TABLE 3-continued

Spectroscopic data of the carboxylic acid amides of the formulae IV* and V*

| Pair of compounds | | IR(film)/γ(cm$^{-1}$)$^{a)}$ | $^1$H—NMR(CDCl$_3$)/δ (ppm) |
|---|---|---|---|
| | | | (s, OCH$_3$), 3.90, 4.03, 4.37, 4.60 (4mc, 4H), 6.97 (d, broad, NH) |
| | 2. | 3400 w, 2950 m, 1745 s, 1670 s | 0.93 (mc, 2CH$_3$), 1.53–1.78 (m, 2CH), 1.79–2.13 (m, 3CH), 2.20–2.36 (m, CH), 3.72 (s, OCH$_3$), 3.83–4.00 (2CH), 4.35 (mc, CH), 4.53–4.67 (m, CH), 7.10 (d, broad, NH) |
| V*(X = O, n = 1, R = (CH$_2$)$_2$SCH$_3$, R' = CH$_3$) | 1. | 2945 m, 1741 s, 1672 s | 1.78–2.35 (m, 6H), 2.10 (s, SCH$_3$), 2.50 (mc, CH$_2$), 3.73 (s, OCH$_3$), 3.90, 3.97, 4.37, 4.69 (4mc, 4H), 7.17 (m, broad, NH) |
| | 2. | As 1. | As 1. |
| V*(X = O, n = 1, R = CH$_2$—C$_6$H$_5$, R' = CH$_3$) | 1. | 3400 w, 2983 m, 1742 s, 1675 s | 1.52–2.32 (m, 4H), 2.97–3.23 (m, CH$_2$), 3.70 (s, OCH$_3$), 3.72–3.93 (m, CH$_2$), 4.30 (mc, 1H), 4.85 (m, 1H), 6.97–7.33 (m, 5H and NH) |
| | 2. | As 1. | 3.73 (s, OCH$_3$), other signals as 1. |
| V*(X = S, n = 1, R = CH(CH$_3$)$_2$, R' = CH$_3$) | 1. | | 0.89–1.02 (m, 2CH$_3$), 1.81–2.41 2.41 (m, 2CH$_2$), 2.96, 3.06 (2mc, 2CH), 3.73 (s, OCH$_3$), 3.97 (mc, CH), 4.51 (mc, CH), 7.40 (d, broad, NH) |
| | 2. | | 3.74 (s, OCH$_3$), 7.45 (d, broad, NH), other signals as 1. |
| V*(X = S, n = 1, R = CH$_3$, R' = CH$_3$) | 1. | | 1.28 (t, J = 8 Hz, CH$_3$), 1.83–2.42 2.42 (m, 4H), 2.90, 3.03 (2mc, CH$_2$), 3.93 (mc, CH), 4.20 (q, J = 8 Hz, CH$_2$), 4.52 (mc, CH), 7.45 (d, broad, NH) |
| | 2. | | 1.29 (t, J = 8 Hz, CH$_3$), 4.21 (q, J = 8 Hz, CH$_2$) |
| V*(X = S, n = 1, R = CH$_2$CH(CH$_3$)$_2$, R' = CH$_3$ | 1. | | 0.92 (mc, 2CH$_3$), 1.50–1.77 (m, 3H), 1.82–2.24 (m, 3H), 2.33 (mc, CH), 2.82, 3.10 (2mc, CH$_2$), 3.73 (s, OCH$_3$), 3.93, 4.57 (2mc, 2CH), 7.26 (d, broad, NH) 3.72 |
| | 2. | | (s, OCH$_3$), 7.38 (d, broad, NH), other signals as 1. |
| V*(X = O, n = 2, R = CH(CH$_3$)$_2$, R' = CH$_3$) | 1. | 3418 w, 2958 m, 1742 s, 1686 s | 0.93 (mc, 2CH$_3$), 1.33–1.67 (m, 2CH$_2$), 1.89 (mc, CH), 2.06 (mc, CH), 2.17 (sept, CH), 3.50 (mc, CH), 3.74 (s, OCH$_3$), 3.83 (mc, CH), 4.09 (mc, CH), 4.53 (mc, CH), 7.00 (d, broad, J = 10 Hz, NH) |
| | 2. | As 1. | 0.95 (mc, 2CH$_3$), 1.28–1.67 (m, 2CH$_2$), 1.90 (mc, CH), 2.12 (mc, CH), 2.17 (sept, CH), 3.49 (mc, CH), 3.74 (s, OCH$_3$), 3.80 (mc, CH), 4.07 (mc, CH), 4.53 (mc, CH), 7.03 (d, broad, J = 10 Hz, NH) |
| V*(X = O, n = 2, R = CH$_2$CH(CH$_3$)$_2$, R' = CH$_3$) | 1. | 3410 m, 2950 s, 1746 s, 1680 s | 0.94 (d, J = 8 Hz, 2CH$_3$), 1.3–1.8 (m, 6H), 1.90 (mc, CH), 2.09 (mc, CH), 3.47, 3.80, 4.07 4.63, (4mc, 4CH), 3.73 (s, OCH$_3$), 6.88 (m, broad, NH) |
| | 2. | As 1. | As 1. |
| V*(X = O, n = 2, R = (CH$_2$)$_2$SCH$_3$, R' = CH$_3$) | 1. | 3390 m, 2942 m 1743 s, 1660 s | 1.28–1.67 (m, 6H), 1.83–2.26 2.26 (m, 2H), 2.10 (s, SCH$_3$), 2.52 (mc, CH$_2$), 3.48, 3.80, 4.07, 4.72 (4mc, 4H), 3.74 (s, OCH$_3$) 7.15 (d, broad, NH) |
| | 2. | As 1. | As 1. |

TABLE 3-continued

Spectroscopic data of the carboxylic acid amides of the formulae IV* and V*

| Pair of compounds | | IR(film)/$\gamma$(cm$^{-1}$)[a] | $^1$H—NMR(CDCl$_3$)/$\delta$ (ppm) |
|---|---|---|---|
| V*(X = S, n = 2, R = CH(CH$_3$)$_2$, R' = CH$_3$) | 1. | 3280 m, 2921 m 1745 s | 0.90 (mc, 2CH$_3$), 1.42–2.98 (m, 10H), 3.40 (mc, CH), 3.78 (s, OCH$_3$), 4.54 (mc, CH), 7.38 (d, broad, NH) |
| | 2. | | 3.80 (s, OCH$_3$), 7.50 (d, broad NH) |
| V*(X = S, n = 2, R = CH$_2$CH(CH$_3$)$_2$, R' = CH$_3$) | 1. | 2950 m, 2923 m 1742 s, 1652 s | 0.99 (mc, 2CH$_3$), 1.51–2.98 (m, 11H), 3.40 (mc, CH), 3.76 (s, OCH$_3$), 4.65 (mc, CH), 7.25 (d, broad, NH) |
| | 2. | | 3.80 (s, OCH$_3$), 7.50 (d, broad, NH) |
| IV*(X = O, n = 1, R = CH(CH$_3$)$_2$, R' = CH$_3$) | 1. | 3275 m, 2959 m, 1742 s, 1654 s | 0.91 (m, 2CH$_3$), 2.18 (m, 3CH), 3.00 (mc, CH), 3.72 (s, OCH$_3$) 3.75–4.00 (m, 3CH), 4.57 (mc, CH), 6.13 (d, broad, NH) |
| | 2. | As 1. | As 1. |
| IV*(X = O, n = 1, R = CH$_2$CH(CH$_3$)$_2$, R' = CH$_3$) | | 3300 s, 2952 m 1748 s, 1795 s | 0.97 (m, 2CH$_3$), 1.74–1.73 (m, 3H), 2.17 (mc, CH$_2$), 2.97 (mc, CH), 3.75 (s, OCH$_3$), 3.78–4.00 (m, 2CH$_2$), 4.62 (mc, CH), 6.38 (d, broad, NH)[c] |

[a] NH—, CH— and CO bands;
[b] For assignment see 1st diastereomer;
[c] Diastereomer mixture

I claim:

1. A process for the preparation of optically active carboxylic acids of the formula I* or II*

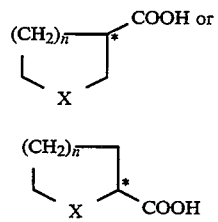

in which X is an oxygen or sulfur atom and n is 1 or 2, which comprises reacting a racemic carboxylic acid I or II or its derivatives, wherein said derivatives are selected from the group consisting of acid halides, esters, anhydrides and amides, with an optically active 2-aminocarboxylic acid ester to give the diastereomeric carboxylic acid amides, separating the diastereomers and, after cleavage of the amide bond, isolating the optically active carboxylic acids of the general formula I* or II*.

2. The process as claimed in claim 1, wherein the racemic carboxylic acid I or II employed is that of the formula

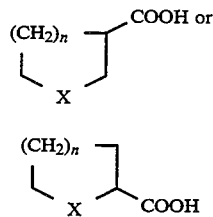

with X=O or S and n=1 or 2.

3. The process as claimed in claim 1, wherein the derivatives of the racemic carboxylic acid I or II employed is its acid chloride.

4. The process as claimed in claim 1, wherein the optically active 2-aminocarboxylic acid ester employed is the (S)- or (R)-2-aminocarboxylic acid ester of the formula III*

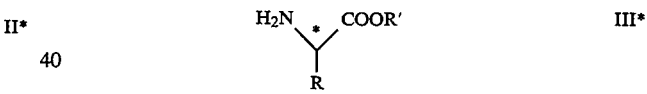

in which the R radical is a linear, branched or cyclic alkyl radical in which a carbon atom is optionally replaced by an oxygen or sulfur atom or by the NR" radical, where R" denotes a methyl or ethyl radical or R is a linear, branched or cyclic alkyl radical which is substituted by the radicals —OH, —SH, —SCH$_3$, —NH$_2$, —COOR''', —CONH$_2$ or by a phenyl group which is optionally substituted by —CH$_3$, —OH or —OCH$_3$, where R''' denotes a methyl, ethyl, n-propyl or i-propyl group, or the radical R denotes a phenyl group which is unsubstituted or substituted by —CH$_3$, —OH or OCH$_3$; and the R' radical is a linear, branched or cyclic C$_{1-20}$-alkyl or C$_{1-20}$ alkoxyalkyl radical which is optionally substituted by a phenyl group, or is a phenyl radical.

5. The process as claimed in claim 4, wherein the R radical is a linear or branched C$_{1-6}$-alkyl radical, —CH$_2$OH, —CHOH(CH$_3$), —CH$_2$SH, —CH$_2$CH$_2$SCH$_3$, —CH$_2$(CH$_2$)$_2$NH$_2$, —CH$_2$(CH$_2$)$_3$NH$_2$, CH$_2$COOR''', —CH$_2$CONH$_2$, —CH$_2$CH$_2$COOR''', —CH$_2$CH$_2$CONH$_2$, phenyl, 4-hydroxy- and 4-methoxyphenyl or benzyl radical.

6. The process as claimed in claim 5, wherein the R radical is —CH$_3$, —CH(CH$_3$)$_2$, —CH$_2$CH(CH$_3$)$_2$, —CH$_2$CH$_2$SCH$_3$, or a benz radical.

7. The process as claimed in claim 4, wherein the R' radical is a linear, branched or cyclic $C_{1-10}$-alkyl or $C_{1-10}$-alkoxyalkyl radical.

8. The process as claimed in claim 4, wherein the R' radical is $-CH_3$, $-CH_2OCH_3$, $-CH_2CH_3$, $-CH_2CH_2CH_3$ or $-CH(CH_3)_2$.

9. The process as claimed in claim 4, wherein the optically active amine component of the formula III* employed is optically active 2-aminocarboxylic acid ester in the S configuration.

10. The process as claimed in claim 4, wherein the diastereomeric carboxylic acid amides have the formulae IV and V

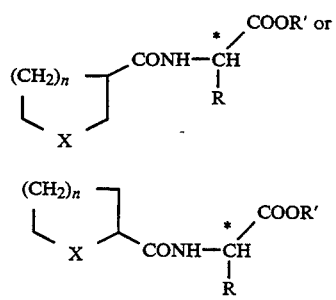

wherein n, X, R and R' are as indicated, and the amides are separated by means of distillation, chromatography or fractional crystallization.

11. The process as claimed in claim 10, wherein the diastereomer separation is carried out by means of distillation.

12. The process as claimed in claim 11, wherein the distillation is carried out under reduced pressure.

13. The process as claimed in claim 10, wherein the diastereomers are separated by means of gas chromatography.

14. The process as claimed in claim 10, wherein the diastereomers are separated by crystallization.

15. The process as claimed in claim 14, wherein the ester groups of the diastereomeric carboxylic acid amides are converted into the free carboxylic acid groups before separation thereof by fractional crystallization 16. The process as claimed in claim 1, wherein to isolate the optically active carboxylic acids of the formula I* or II*, the amide bond is cleaved in the aqueous phase at a temperature of about 80° to about 200° C. after the diastereomer separation.

17. The process as claimed in claim 16, wherein the cleavage is carried out in 1N hydrochloric acid at a temperature between about 100° and about 120° C.

18. The process as claimed in claim 16, wherein metal salts are also added in an amount of about 1 to about 20 mol %, relative to the isolated fraction of the carboxylic acid amides, to accelerate the cleavage reaction.

19. The process as claimed in claim 1, wherein, to prepare the pure optically active carboxylic acids of the formula I* or II*, the reaction mixture is evaporated after cleavage, the residue is digested in an inert solvent to recover the optically active 2-aminocarboxylic acid and the organic phase is fractionally distilled after evaporation of the solvent.

20. Optically active carboxylic acid amides of the formula IV* or V*

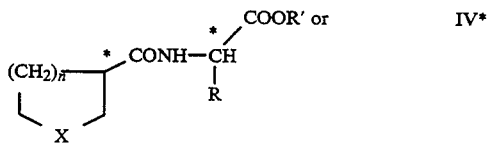

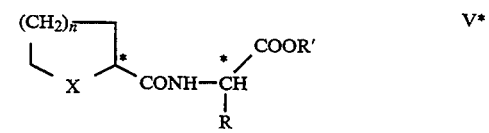

wherein $n=1$ or 2, $X=O$ or S, and R and R' are as defined in claim 4.

21. Optically active carboxylic acid amides of the formula IV* or V*

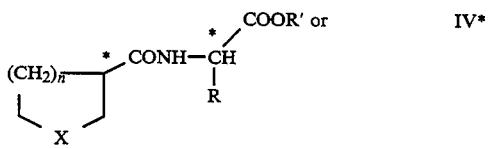

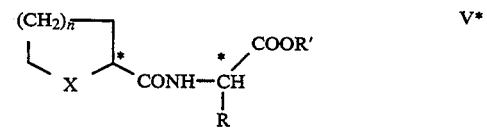

wherein $n=1$ or 2, $X=S$ or O, R is $-CH_3$, $-CH(CH_3)_2$, $-CH_2CH(CH_3)_2$, $-CH_2CH_2SCH_3$, or a benzyl radical, and R' is $-CH_3$, $-CH_2OCH_3$, $-CH_2CH_3$, $-CH_2CH_2CH_3$ or $-CH(CH_3)_2$.

22. The optically active carboxylic acid amides of claim 21, wherein $n=2$, $X=S$, R is $-CH_3$, $-CH(CH_3)_2$, $-CH_2CH(CH_3)_2$, $-CH_2CH_2SCH_3$, or a benzyl radical, and R' is $-CH_3$, $-CH_2OCH_3$, $-CH_2CH_3$, $CH_2CH_2CH_3$ or $CH(CH_3)_2$.

23. The optically active carboxylic acid amides of claim 20 wherein $n=1$, $X=O$, R is $-CH_3$, $-CH(CH_3)_2$, $-CH_2CH(CH_3)_2$, $-CH_2CH_2SCH_3$, or a benzyl radical, and R' is $-CH_3$, $-CH_2OCH_3$, $-CH_2CH_3$—$CH_2CH_2CH_3$ or $-CH(CH_3)_2$.

24. The optically active carboxylic acid amides of claim 21 wherein $n=2$, $X=O$, R is $-CH_3$, $-CH(CH_3)_2$, $-CH_2CH(CH_3)_2$, $-CH_2CH_2SCH_3$, or a benzyl radical, and R' is $-CH_3$, $-CH_2OCH_3$, $-CH_2CH_3$, $-CH_2CH_2CH_3$ OR $-CH(CH_3)_2$.

* * * * *